US012575971B2

(12) United States Patent      (10) Patent No.:    US 12,575,971 B2
Ichikawa et al.                  (45) Date of Patent:      Mar. 17, 2026

(54) OPHTHALMIC SURGERY INSTRUMENT, INTRAOCULAR EXCISION MEMBER, AND MANUFACTURING METHOD THEREFOR

(71) Applicant: TRABECTOR CO., INC., Nagoya (JP)

(72) Inventors: Kazuo Ichikawa, Nagoya (JP); Hiroto Toda, Tokai (JP)

(73) Assignee: TRABECTOR CO., INC., Nagoya (JP)

( * ) Notice: Subject to any disclaimer, the term of this patent is extended or adjusted under 35 U.S.C. 154(b) by 108 days.

(21) Appl. No.: 18/760,807

(22) Filed: Jul. 1, 2024

(65) Prior Publication Data

US 2025/0073069 A1     Mar. 6, 2025

(30) Foreign Application Priority Data

Aug. 28, 2023    (JP) ................................. 2023-137782

(51) Int. Cl.
    *A61F 9/007*           (2006.01)
(52) U.S. Cl.
    CPC ................................. *A61F 9/00763* (2013.01)
(58) Field of Classification Search
    CPC .. A61F 9/007; A61F 9/00736; A61F 9/00745; A61F 9/00763; A61F 9/00781
    See application file for complete search history.

(56) References Cited

U.S. PATENT DOCUMENTS

| | | | | |
|---|---|---|---|---|
| 4,652,255 A | * | 3/1987 | Martinez | ............. A61F 9/00736 604/27 |
| 5,047,008 A | * | 9/1991 | de Juan, Jr. | ......... A61F 9/00763 606/171 |
| 8,016,843 B2 | * | 9/2011 | Escaf | .................. A61F 9/00745 606/166 |

(Continued)

FOREIGN PATENT DOCUMENTS

| | | |
|---|---|---|
| CN | 113081472 A | 7/2021 |
| JP | 2010-500073 A | 1/2010 |

(Continued)

OTHER PUBLICATIONS

Jan. 14, 2025 European Search Report issued in European Patent Application No. 24196604.3.

(Continued)

*Primary Examiner* — Ryan J. Severson
(74) *Attorney, Agent, or Firm* — OLIFF PLC

(57) ABSTRACT

Provided is an ophthalmic surgery instrument that allows an instrument suitable for excising a trabecular meshwork to be configured and allows a grip portion to be used for both first ophthalmic surgery such as trabeculectomy and second ophthalmic surgery. A first passage and a second passage for performing suction or supply of a perfusate are formed in a grip portion of an ophthalmic surgery instrument. An internal thread portion is formed at a tip end of the grip portion. A tip end member for first ophthalmic surgery has a single passage therein, and has a bent-shaped blade portion and an opening of the passage at a tip end thereof. The tip end (Continued)

member for first ophthalmic surgery and a tip end member for second ophthalmic surgery are selectively screwable to the internal thread portion.

10 Claims, 6 Drawing Sheets

(56) References Cited

U.S. PATENT DOCUMENTS

| | | | | |
|---|---|---|---|---|
| 10,463,385 | B2 * | 11/2019 | Ichikawa | A61F 9/00763 |
| 11,806,281 | B2 * | 11/2023 | Ichikawa | A61F 9/00736 |
| 2006/0241580 | A1 * | 10/2006 | Mittelstein | A61B 18/1482 606/41 |
| 2007/0060926 | A1 | 3/2007 | Escaf | |
| 2014/0194916 | A1 * | 7/2014 | Ichikawa | A61B 17/3203 606/180 |

| | | | | |
|---|---|---|---|---|
| 2017/0311970 | A1 * | 11/2017 | Ichikawa | A61F 9/00781 |
| 2021/0275353 | A1 | 9/2021 | Ichikawa et al. | |
| 2025/0073069 | A1 * | 3/2025 | Ichikawa | A61F 9/00763 |

FOREIGN PATENT DOCUMENTS

| | | | |
|---|---|---|---|
| JP | 2013-52168 | A | 3/2013 |
| JP | 2018-537214 | A | 12/2018 |
| JP | 6934685 | B2 | 9/2021 |
| WO | 2008/017909 | A1 | 2/2008 |
| WO | 2017/103778 | A1 | 6/2017 |
| WO | 2021/113399 | A9 | 7/2022 |

OTHER PUBLICATIONS

Sep. 20, 2023 Office Action issued in Japanese Patent Application No. 2023-137782.

* cited by examiner

OPHTHALMIC SURGERY INSTRUMENT, INTRAOCULAR EXCISION MEMBER, AND MANUFACTURING METHOD THEREFOR

RELATED APPLICATIONS

This application claims the priority of Japanese Patent Application No. 2023-137782 filed on Aug. 28, 2023, which issued as Japanese Patent No. 7411297 on Dec. 27, 2023. The disclosures of the prior applications are incorporated by reference in their entirety.

BACKGROUND OF THE INVENTION

Field of the Invention

This disclosure relates to an ophthalmic surgery instrument.

Description of Related Art

Japanese Patent No. 6934685 discloses an ophthalmic surgery instrument used for trabeculectomy as glaucoma surgery. The instrument of Japanese Patent No. 6934685 includes a rod-shaped portion having a single passage formed therein. The rod-shaped portion has a bent portion and an opening of the passage at a tip end thereof. A to-be-excised part (trabecular meshwork) in an eye is excised with the bent portion. In addition, it is indicated that a liquid is caused to flow out through the opening of the rod-shaped portion or the excised part is sucked through the opening into the passage.

The instrument of Japanese Patent No. 6934685 has, at a tip end thereof, the bent portion (blade portion) having a bent shape, and is assumed to be applied to surgery to excise a trabecular meshwork or the like with the bent portion. Thus, it is difficult to apply this instrument to other ophthalmic surgery in which the bent portion is not used.

This disclosure has been made in view of the aforementioned circumstances, and an object of this disclosure is to provide an ophthalmic surgery instrument or intraocular excision member that allows an instrument suitable for excising a trabecular meshwork to be configured and allows a grip portion to be used for both first ophthalmic surgery such as trabeculectomy and second ophthalmic surgery different from the first ophthalmic surgery.

SUMMARY OF THE INVENTION

An ophthalmic surgery instrument of this disclosure includes:
  a dual-use grip portion having a first passage and a second passage separately formed therein for performing suction and supply of a perfusate, having a first opening, which is an opening of the first passage, and a second opening, which is an opening of the second passage, formed at a tip end thereof, and used for both first ophthalmic surgery, which is glaucoma surgery, and second ophthalmic surgery different from glaucoma surgery; and
  an excision member detachably provided at the tip end of the dual-use grip portion, having a single passage formed therein so as to be connected to the first passage, having a bent-shaped blade portion and an opening of the single passage at a tip end thereof, and used to excise a part in an eye in the first ophthalmic surgery, wherein the dual-use grip portion has, at the tip end thereof, a thread portion to which the excision member is attached, and
  the thread portion is formed so as to be screwable to a tip end member for treating an inside of an eye in the second ophthalmic surgery instead of the excision member.

According to this, since the excision member is attachable to and detachable from the dual-use grip portion, and the tip end member for treating the inside of the eye in the second ophthalmic surgery is screwable to the thread portion of the dual-use grip portion instead of the excision member, the grip portion can be used for both the first ophthalmic surgery and the second ophthalmic surgery, which improves convenience by the dual use of the grip portion. In addition, since the excision member has the bent-shaped blade portion, a trabecular meshwork can be excised with the blade portion. In this case, the first ophthalmic surgery is glaucoma surgery (specifically, trabeculectomy). When the excision member is attached to the dual-use grip portion, the first passage of the dual-use grip portion and the single passage of the excision member are connected to each other, so that, for example, an excised part (e.g., trabecular meshwork) in the eye can be sucked, or the perfusate can be supplied into the eye, via the first passage and the single passage. Moreover, since the passage of the excision member is a single passage, the structure of the excision member can be simplified. Furthermore, since the dual-use grip portion is screwable to the tip end member for treating the inside of the eye in the second ophthalmic surgery (e.g., cataract surgery) instead of the excision member, an instrument to be used for the second ophthalmic surgery can be configured by attaching the tip end member to the dual-use grip portion. Moreover, an instrument for the first ophthalmic surgery can be configured by attaching the excision member for the first ophthalmic surgery to the dual-use grip portion instead of the tip end member for the second ophthalmic surgery. Thus, by having the dual-use grip portion, the excision member, and the tip end member, an ophthalmic surgery instrument that can be used for both the first ophthalmic surgery and the second ophthalmic surgery can be configured.

An intraocular excision member of this disclosure is an excision member having a single passage formed therein, having a thread portion at a base end thereof, having a bent-shaped blade portion and an opening of the passage at a tip end thereof, and used to excise a part in an eye in first ophthalmic surgery which is glaucoma surgery, wherein
  the thread portion is detachably attached to a grip portion held by a user,
  the grip portion is a dual-use grip portion having a first passage and a second passage separately formed therein for performing suction or supply of a perfusate, having a first opening, which is an opening of the first passage, and a second opening, which is an opening of the second passage, at a tip end thereof, and used for both the first ophthalmic surgery and second ophthalmic surgery different from glaucoma surgery,
  the grip portion has a thread portion to which the thread portion of the excision member is attached,
  the thread portion of the grip portion is formed so as to be screwable to a tip end member for treating an inside of an eye in the second ophthalmic surgery instead of the excision member, and
  the passage of the excision member is connected to the first passage in a state where the excision member is attached to the grip portion.

According to this, since the intraocular excision member of this disclosure used for the first ophthalmic surgery can be attached to the dual-use grip portion which can also be used for the second ophthalmic surgery, it is possible to configure an instrument suitable for excising a trabecular meshwork and to improve convenience by the dual use of the grip portion.

An intraocular excision member manufacturing method of this disclosure includes:

a preparation step of preparing a needle member which is not bent at a tip end thereof, has therein a passage penetrating from a base end to the tip end thereof, and has an end surface formed in a sharp shape around an opening on the tip end side and inclined with respect to a central axis of the needle member; and a bending step of bending the end surface of the needle member to form the blade portion.

Thus, by bending the tip end of the needle member, the intraocular excision member of this disclosure can be easily obtained.

DETAILED DESCRIPTION

Figure 1:
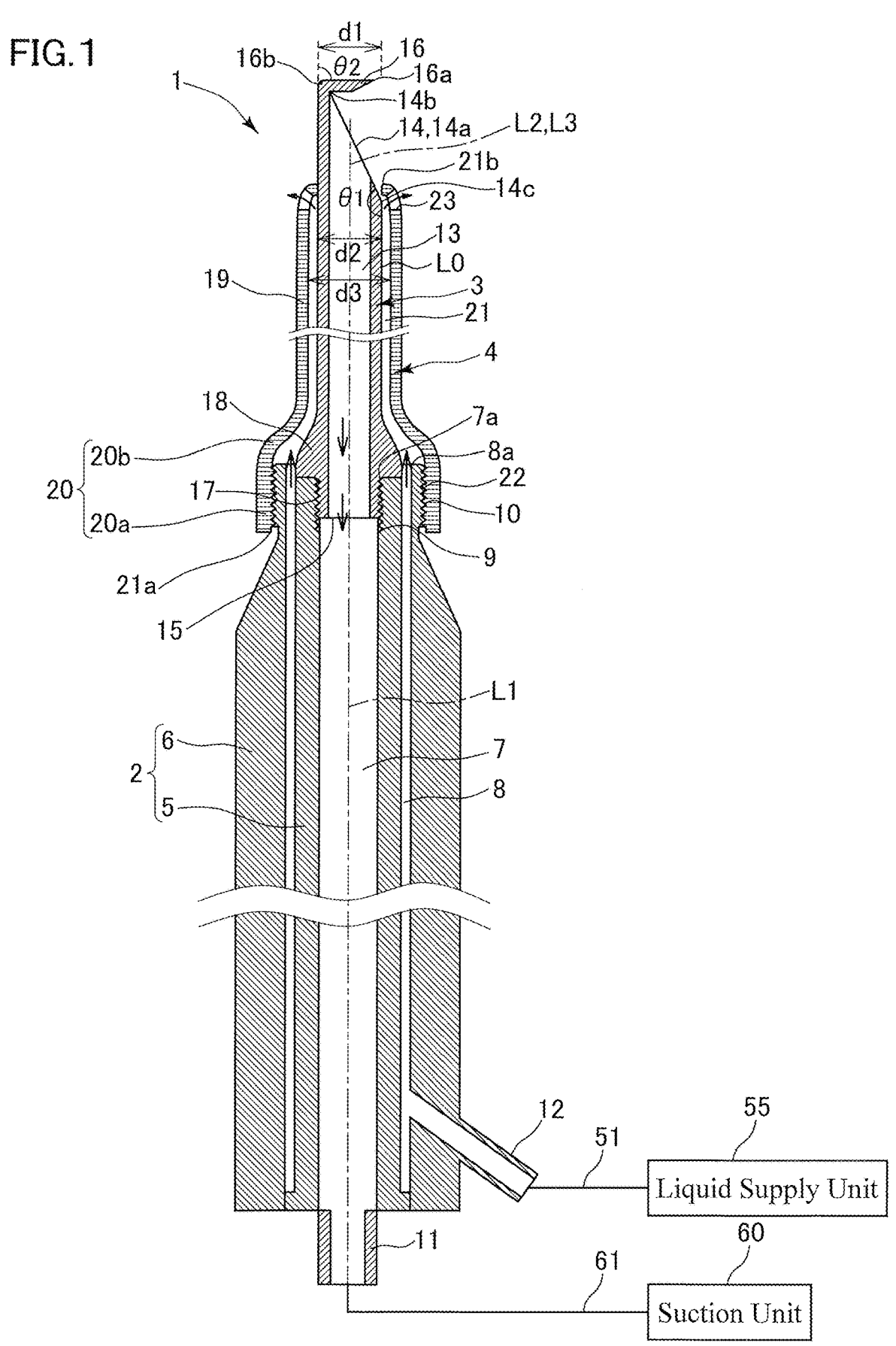
FIG. 1 shows a cross-section of an ophthalmic surgery instrument cut so as to include a central axis thereof in the cross-section.

Hereinafter, an embodiment of this disclosure will be described with reference to the drawings. An ophthalmic surgery instrument 1 shown in FIG. 1 is used, for example, for surgery to excise a trabecular meshwork (first ophthalmic surgery) as a treatment for glaucoma. The instrument 1 includes a grip portion 2, a tip end member 3 as an intraocular excision member, and a sleeve 4 as an outer member.

The grip portion 2 is a portion to be held by a practitioner. The grip portion 2 is a dual-use grip portion that can be used for both the first ophthalmic surgery and second ophthalmic surgery (e.g., cataract surgery). The grip portion 2 is formed in a rod shape. Specifically, the grip portion 2 includes an inner tubular portion 5 and an outer tubular portion 6. The inner tubular portion 5 is formed in a tubular shape having a linearly extending first passage 7 formed therein. The first passage 7 is located on a central axis L1 of the grip portion 2. In other words, the central axis of the first passage 7 defines the central axis L1 of the grip portion 2. An opening 7a (first opening) of the first passage 7 is formed at a tip end of the inner tubular portion 5. The first passage 7 is, for example, a passage for sucking an excised part (e.g., trabecular meshwork) in the eye or drainage or the like from the inside of the eye during ophthalmic surgery. That is, the sucked matter such as the excised part flows into the first passage 7.

The outer tubular portion 6 is formed in a tubular shape that is coaxial with the inner tubular portion 5 and has a larger diameter than the inner tubular portion 5, so as to surround the outer side of the inner tubular portion 5. A second passage 8 is formed inside the outer tubular portion 6 so as to extend linearly in the direction of the central axis L1. The second passage 8 is formed, for example, so as to surround the outer side of the inner tubular portion 5. That is, a cross-section, perpendicular to the central axis L1, of the second passage 8 is annular, for example. An opening 8a (second opening) of the second passage 8 is formed at a tip end of the outer tubular portion 6. The second passage 8 is used, for example, as a passage through which a perfusate to be supplied into the eye (specifically, the anterior chamber) during ophthalmic surgery is caused to flow.

The grip portion 2 has an internal thread portion 9 on a tip end side thereof. The internal thread portion 9 is formed on the inner surface on the tip end side (opening 7a side) of the first passage 7.

The grip portion 2 has an attachment-target portion 10 to which the sleeve 4 is detachably attached, on the tip end side thereof. The attachment-target portion 10 is formed on the outer surface on the tip end side (opening 8a side) of the outer tubular portion 6. The attachment-target portion 10 is formed so as to allow the attachment position of the sleeve 4 in the direction of the axis L1 to be adjusted. Specifically, the attachment-target portion 10 is formed, for example, in a shape surrounding the entire circumference around the axis L1 and having a plurality of engagement portions (protrusions or grooves) in the direction of the axis L1. More specifically, the attachment-target portion 10 may be, for example, an external thread portion composed of a helical protrusion or groove that advances in the direction of the axis L1 while extending around the axis L1.

The grip portion 2 has a first port 11 and a second port 12 on a base end side thereof. The first port 11 is connected to the first passage 7. The first port 11 is connected, for example, to a suction unit 60 (in other words, suction device) via a tube 61. The second port 12 is connected to the second passage 8. The second port 12 is connected, for example, to a liquid supply unit 55 (in other words, liquid supply tank) which supplies the perfusate, via a tube 51. The liquid supply unit 55 may be connected to the first port 11, and the suction unit 60 may be connected to the second port 12. In this case, the first passage 7 functions as a passage through which the perfusate is caused to flow, and the second passage 8 functions as a suction passage.

The grip portion 2 is located as a whole outside the eye during ophthalmic surgery and does not have a portion that is inserted into the eye. The first opening 7a and the second opening 8a are located outside the eye during ophthalmic surgery.

The tip end member 3 is an excision member that is inserted into the eye during the first ophthalmic surgery (e.g., glaucoma surgery) to excise a part (e.g., trabecular meshwork) in the eye. The tip end member 3 is formed in an elongated shape, specifically, in a cylindrical shape having a linearly extending single passage 13 therein. The central axis of the passage 13 constitutes a central axis L2 of the tip end member 3. The tip end member 3 has openings 14 and 15 of the passage 13 at a tip end and a base end thereof, respectively.

The tip end opening 14 is inclined with respect to the central axis L2 of the tip end member 3. That is, the tip end opening 14 is formed in a shape in which the tip end opening 14 gradually advances in the direction of the axis L2 as extending from one end side toward another end side in the radial direction of the tip end member 3. More specifically, the tip end opening 14 gradually advances toward the upper side of the drawing sheet of FIG. 1 (the side approaching a bent portion 16 described later, the side away from a base end 15 of the tip end member 3) as extending from the right side toward the left side of the drawing sheet of FIG. 1 in the radial direction.

Here, a point 14c, closest to the base end 15 side (see FIG. 1), on an end surface 14a forming the tip end opening 14 (hereinafter referred to as tip end opening surface) (see FIG. 2) is defined as lower end. An angle θ1 formed between a contour line L0 of the tip end member 3 linearly extending parallel to the central axis L2 from the lower end 14c and a tip end opening surface 14a as seen in the cross-section in FIG. 1 is greater than 90° and less than 180°. The angle θ1 is preferably 120° or greater and 160° or less. If the angle θ1 is 120° or greater, the length from the lower end 14c through a corner portion 16b (base end) of the bent portion 16 to a tip end 16a of the bent portion 16 can be long, and the bent portion 16 can be easily formed in a manufacturing process of the tip end member 3. If the angle θ1 is 160° or less, the interval between the lower end 14c and the bent portion 16 can be inhibited from becoming excessively large, and a part (e.g., trabecular meshwork) excised by the bent portion 16 during ophthalmic surgery can be easily sucked into the passage 13 through the tip end opening 14.

The tip end opening surface 14a (see FIG. 2) may be formed in a sharp shape, that is, as a blade surface. In this case, the tip end opening surface 14a forms a blade portion capable of excising a part in an eye. The tip end opening surface 14a may be formed in a non-sharp shape (obtuse angle shape).

The central axis L2 intersects the tip end opening 14. In addition, the central axis L2 is located between an upper end 14b (portion farthest from the base end 15) of the tip end opening surface 14a and the lower end 14c (portion closest to the base end 15) of the tip end opening surface 14a as seen in the cross-section in FIG. 1 including the central axis L2 therein. Moreover, a line drawn by the tip end opening surface 14a from the lower end 14c to the upper end 14b is, for example, a straight line, as seen in the cross-section in FIG. 1, but may be a curved line or composed of a plurality of straight lines having different inclinations.

The tip end member 3 has, at the tip end thereof, the bent portion 16 having a bent shape with respect to the direction of the central axis L2 (in other words, the direction in which the passage 13 extends). The bent portion 16 is formed in a substantially triangular shape as seen in plan views in FIG. 2 and FIG. 3 to which the axis L2 is orthogonal. The bent portion 16 forms a blade portion for excising a part in an eye. Specifically, the tip end 16a (see FIG. 1 to FIG. 3) of the bent portion 16 is formed in a sharp shape (acute angle shape). The tip end 16a may be formed in a non-sharp shape (obtuse angle shape, rounded shape).

Figure 3:
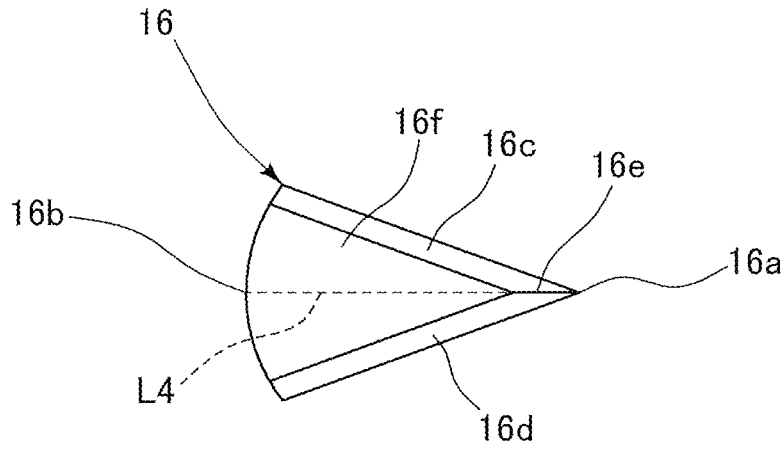
FIG. 3 is a bottom view of a bent portion of the tip end member as seen from the lower side of the drawing sheet of FIG. 1.

The bent portion 16 has a first blade surface 16c and a second blade surface 16d as shown in FIG. 3. These blade surfaces 16c and 16d extend from a base end 16b toward a tip end 16a of the bent portion 16. In addition, the interval between the blade surfaces 16c and 16d gradually decreases from the base end 16b toward the tip end 16a. The blade surfaces 16c and 16d are connected to each other on the tip end 16a side. A straight boundary line 16e between the blade surfaces 16c and 16d appears on the tip end 16a side. The thickness (thickness in a direction perpendicular to the drawing sheet of FIG. 3) of a bent portion 16 at the boundary line 16e gradually decreases as the distance to the tip end 16a decreases.

Figure 2:
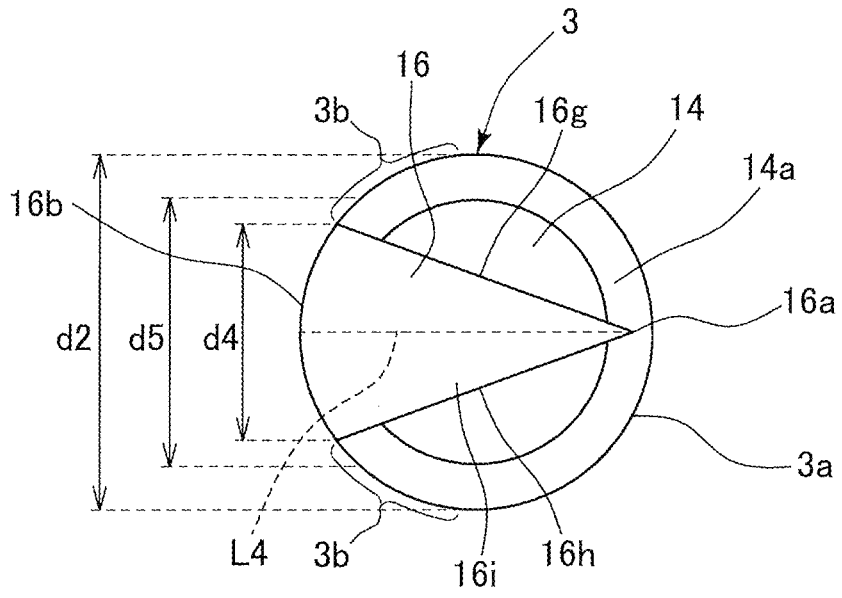
FIG. 2 is a top view of a tip end member as seen from the upper side of the drawing sheet of FIG. 1.

The lengths of both blade surfaces 16c and 16d from the base end 16b to the tip end 16a may be the same as each other. A virtual line L4 connecting the midpoint of the base end 16b and the tip end 16a of the bent portion 16 as seen in the direction of FIG. 3 is referred to as bent portion center line. The blade surfaces 16c and 16d may be formed in a shape that is line-symmetrical with respect to the bent portion center line L4. The blade surfaces 16c and 16d face the tip end opening 14 side. As shown in FIG. 2, no blade surface is formed in an upper surface 16i (surface on the side opposite to the tip end opening 14 side) of the bent portion 16.

As shown in FIG. 3, the bent portion 16 has an intermediate surface 16f between the blade surfaces 16c and 16d. The intermediate surface 16f is formed in a substantially triangular shape. The intermediate surface 16f is not curved, for example, at the position of the bent portion center line L4, that is, may extend linearly along the bent portion center line L4. The intermediate surface 16f may be curved along a direction perpendicular to the bent portion center line L4, or may have a flat shape.

As shown in FIG. 1 and FIG. 2, the base end 16b of the bent portion 16 is located at one end in the radial direction of a body (a portion forming the passage 13, other than the bent portion 16) of the tip end member 3.

A width d1 (see FIG. 1) of the bent portion 16 from the base end 16b to the tip end 16a in a direction perpendicular to the axis L2 may be equal to an outer diameter d2 (see FIG. 1) of the body of the tip end member 3, may be slightly larger than the outer diameter d2, or may be slightly smaller than the outer diameter d2. In other words, as seen in the plan view in FIG. 2, the tip end 16a may be provided at a position that coincides with an outer surface 3a of the body of the tip end member 3, may be located slightly outward of the outer surface 3a, or may be located slightly inward of the outer surface 3a. The tip end 16a may be located on the side farther from the base end 16b than the axis L2 (on the right side with respect to the axis L2 in the drawing sheet of FIG. 1).

The width d1 of the bent portion 16 is smaller than an inner diameter d3 (see FIG. 1) on the tip end side of the sleeve 4. The tip end 16a may be located inward of the inner diameter d3 of the sleeve 4. Furthermore, the width d1 of the bent portion 16 may be smaller than the diameter of a tip end opening 21b of the sleeve 4, may be equal to this diameter, or may be slightly larger than this diameter. When the width d1 of the bent portion 16 and the position of the tip end 16a are determined as described above, the sleeve 4 can be easily attached to the outer side of the tip end member 3, and a part in an eye can be easily excised.

As seen in the plan view in FIG. 2 to which the central axis L2 of the tip end member 3 is orthogonal, a maximum width d4 of the bent portion 16 in a direction perpendicular to the above center line L4 may be smaller than the outer diameter d2 of the body of the tip end member 3. The bent portion 16 has edge portions 16g and 16h connecting the base end 16b and the tip end 16a of the bent portion 16 as seen in the plan view in FIG. 2. The maximum width d4 is a maximum width between both edge portions 16g and 16h, that is, a width of the base end 16*b* in the direction perpendicular to the center line L4 as seen in the plan view in FIG. 2.

The tip end side of the body (portion forming the passage 13, other than the bent portion 16) of the tip end member 3 has a narrow portion 3*b* (see FIG. 2) having an outline width d5, in the up-down direction of the drawing sheet of FIG. 2, which gradually decreases toward the bent portion 16 side in the direction of the axis L2. The outline width d5 is also an outline width in a direction orthogonal to the drawing sheet of FIG. 1. The width d5 is a width in a direction perpendicular to both the central axis L2 of the tip end member 3 and the center line L4 of the bent portion 16, that is, a width in the direction orthogonal to the drawing sheet of FIG. 1. The width d5 of the narrow portion 3*b* is smaller than the outer diameter d2 of the body of the tip end member 3. In addition, the width d5 is equal to a width d4 of the bent portion 16 at the position of a connection portion 16*b* with the bent portion 16 (base end of the bent portion 16).

The bent portion 16 is located above the tip end opening 14 (on the side far from the base end 15 in the direction of the axis L2). The bent portion 16 is provided so as to face the tip end opening 14 in the direction of the axis L2. In addition, the bent portion 16 is provided so as to overlap a portion of the tip end opening 14 as seen in the plan view in FIG. 2 to which the axis L2 is orthogonal. In other words, the bent portion 16 is provided at a position that the axis L2 intersects. Specifically, the axis L2 intersects the above intermediate surface 16*f* (see FIG. 3).

An angle θ2 (see FIG. 1) of the bent portion 16 with respect to the axis L2 is, for example, 60° or greater and 120° or less. FIG. 1 shows an example in which the angle θ2 is 90°. With this angle θ2, it can be made easier to excise a trabecular meshwork when the bent portion 16 is moved so as to draw an arc trajectory along the outer circumference of the anterior chamber.

The tip end member 3 has an external thread portion 17 on the base end opening 15 side. The external thread portion 17 is inserted into the first passage 7 through the first opening 7*a* of the grip portion 2 and screwed to the internal thread portion 9. The base end opening 15 is located in the first passage 7. The passage 13 of the tip end member 3 and the passage 7 of the grip portion 2 are connected to each other via the base end opening 15.

As shown in FIG. 1, the tip end member 3 has a protruding portion 18 protruding laterally from an end portion on the side of the external thread portion 17 opposite to the base end opening 15. The protruding portion 18 is in contact with the end surface of the inner tubular portion 5 of the grip portion 2.

The tip end member 3 is provided so as to be detachably attached to the grip portion 2 by means of the external thread portion 17. That is, the tip end member 3 can be detached from the grip portion 2. A portion from the tip end of the tip end member 3 protrudes from the tip end opening 21*b* of the sleeve 4. Specifically, the bent portion 16 and the tip end opening 14 of the tip end member 3 protrude from the tip end opening 21*b* of the sleeve 4. The portion of the tip end member 3 other than the tip end side is provided in the sleeve 4. The lower end 14*c* side of the tip end opening 14 may be provided in the sleeve 4. In a state where the tip end member 3 is attached to the grip portion 2, the central axis L2 of the tip end member 3 coincides with the central axis L1 of the grip portion 2.

The sleeve 4 is detachably attached to the grip portion 2 so as to cover the outer side of the tip end member 3. The sleeve 4 is formed of a flexible (that is, elastic) material such as silicone rubber. The sleeve 4 easily deforms when an external force is applied, and returns to its original shape when the external force is released.

The sleeve 4 has a small-diameter portion 19 and a large-diameter portion 20 provided on the same axis L3 with each other. Cross-sections, perpendicular to the central axis L3, of the small-diameter portion 19 and the large-diameter portion 20 are annular. The small-diameter portion 19 and the large-diameter portion 20 form a space 21 therein. The space 21 is formed so as to have a diameter larger than the outer diameter of the tip end member 3 such that a gap serving as a passage for the perfusate is formed between the outer surface of the tip end member 3 and the inner surface of the sleeve 4. Hereinafter, the space 21 is sometimes referred to as passage. The passage 21 formed between sleeve 4 and the tip end member 3 is formed in an annular shape surrounding the tip end member 3 as seen in a cross-section perpendicular to the axis L3.

Openings 21*a* and 21*b* of the space 21 are formed on both ends of the sleeve 4 in the direction of the central axis L3, respectively. Hereinafter, the opening 21*a* on the large-diameter portion 20 side is referred to as base end opening, and the opening 21*b* on the small-diameter portion 19 side is referred to as tip end opening. The tip end opening 21*b* is formed so as to have a smaller diameter than the base end opening 21*a*. The tip end opening 21*b* is smaller than the inner diameter d3 of the small-diameter portion 19. The diameter of the tip end opening 21*b* is equal to the outer diameter of the tip end member 3. The tip end opening 21*b* is a hole for causing the tip end side (bent portion 16) of the tip end member 3 to protrude from the sleeve 4. The tip end opening 21*b* is set to a diameter that allows the tip end side of the tip end member 3 to pass therethrough. In a state where the sleeve 4 is attached to the outer side of the tip end member 3, the outer circumferential edge of the tip end opening 21*b* may be in contact with the outer circumferential surface of the tip end member 3.

The small-diameter portion 19 is formed in a tubular shape having a smaller diameter than the large-diameter portion 20. A hole 23 is formed on the tip end side of the small-diameter portion 19 so as to be connected to the inner space 21. The hole 23 is formed separately from the tip end opening 21*b*, and is shaped so as to penetrate between the outer circumferential surface and the inner circumferential surface of the small-diameter portion 19 below the tip end opening 21*b*. The hole 23 may be formed at a plurality of locations in the circumferential direction around the axis L3 (e.g., two locations on sides opposite to each other by) 180°, or may be formed at one location. The hole 23 serves as an outlet for the perfusate. The small-diameter portion 19 is a portion that is inserted into the eye during ophthalmic surgery.

The large-diameter portion 20 is a portion located outside the eye during ophthalmic surgery. The large-diameter portion 20 has a first portion 20*a* located on the base end opening 21*a* side, and a second portion 20*b* located on the small-diameter portion 19 side. The first portion 20*a* is a constant diameter portion whose inner diameter and outer diameter do not change along the direction of the axis L3. The second portion 20*b* is formed in a shape in which the inner diameter and the outer diameter thereof gradually decrease toward a direction approaching the small-diameter portion 19 in the direction of the axis L3.

The first portion 20*a* has, on the inner surface thereof, an attachment portion 22 which is detachably attached to the attachment-target portion 10 of the grip portion 2. The attachment portion 22 is formed so as to allow the attachment position of the sleeve 4 in the direction of the axis L3 to be adjusted. Specifically, the attachment portion 22 is formed, for example, in a shape surrounding the entire circumference around the axis L3 and having a plurality of engagement portions (protrusions or grooves) in the direction of the axis L3. More specifically, the attachment portion 22 may be, for example, an internal thread portion composed of a helical protrusion or groove that advances in the direction of the axis L3 while extending around the axis L3.

In the case where the attachment-target portion 10 of the grip portion 2 has a plurality of engagement portions (protrusions or grooves) in the direction of the axis L1 of the grip portion 2, the attachment portion 22 of the sleeve 4 may have a shape, other than an internal thread portion, which engages any of the plurality of engagement portions. Conversely, in the case where the attachment portion 22 of the sleeve 4 has a plurality of engagement portions (protrusions or grooves) in the direction of the axis L3 of the sleeve 4, the attachment-target portion 10 of the grip portion 2 may have a shape, other than an external thread portion, which engages any of the plurality of engagement portions.

The sleeve 4 is attached to the grip portion 2 such that a portion on the tip end side of the grip portion 2 is inserted into the large-diameter portion 20, while covering the tip end member 3. In a state where the sleeve 4 is attached to the grip portion 2, the second passage 8 of the grip portion 2 and the passage 21 of the sleeve 4 are connected to each other via the second opening 8a of the grip portion 2. In addition, in a state where the sleeve 4 is attached to the grip portion 2, the central axis L3 of the sleeve 4 coincides with the central axis L2 of the tip end member 3.

The sleeve 4 may be a member that is used for both the first ophthalmic surgery (e.g., glaucoma surgery) and the second ophthalmic surgery (e.g., cataract surgery). That is, when a tip end member 30 for the second ophthalmic surgery (see FIG. 4 and FIG. 5) described later is attached to the grip portion 2 instead of the tip end member 3, the sleeve 4 may be attachable to the grip portion 2 so as to cover the outer side of the tip end member 30. A sleeve (not shown) for the second ophthalmic surgery having a shape different from that of the sleeve 4 for the first ophthalmic surgery may be provided.

Figure 4:
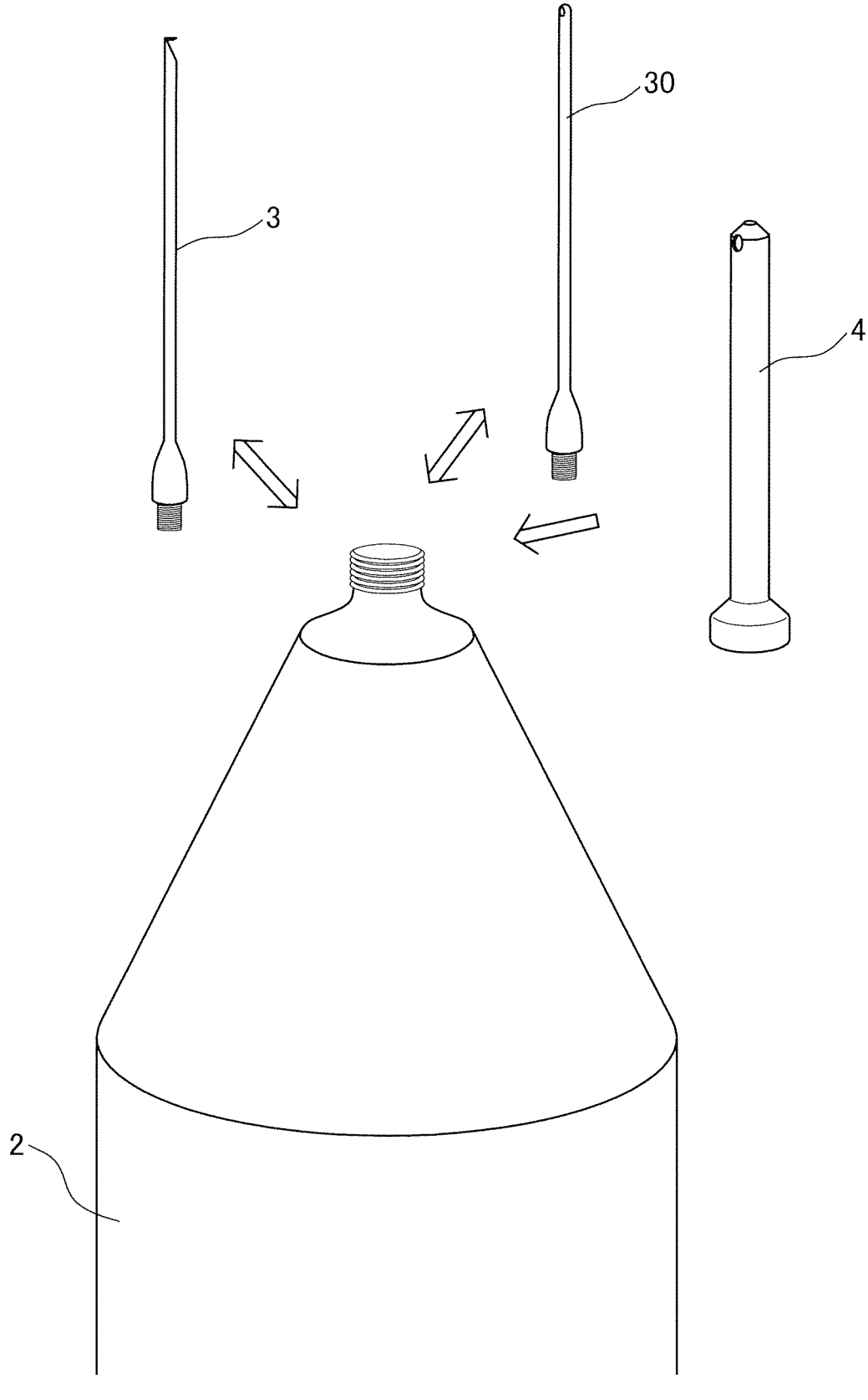
FIG. 4 is a perspective view of a tip end side of a grip portion, and a tip end member for first ophthalmic surgery, a tip end member for second ophthalmic surgery, and a sleeve to be attached to the grip portion.

As shown in FIG. 4, the tip end member 3 for the first ophthalmic surgery and the tip end member 30 for the second ophthalmic surgery described above are selectively attachable to the grip portion 2. That is, the tip end member 30 is attachable to the grip portion 2 instead of the tip end member 3, and conversely, the tip end member 3 is attachable to the grip portion 2 instead of the tip end member 30.

The tip end member 30 is, for example, a member for treating the inside of the eye in cataract surgery. In cataract surgery, for example, a first treatment in which the inside of the crystalline lens is crushed and emulsified by ultrasonic waves while perfusion water is supplied to the treatment part, and the emulsified tissue in the crystalline lens is sucked together with the perfusion water, is performed. After most of the crystalline lens is removed in the first treatment, a second treatment in which the remaining tissue such as cortex of crystalline lens capsule is sucked while the perfusion water is sent, is performed. The tip end member 30 may be a member for performing the first treatment (crush, perfusion, and suction) or the second treatment (perfusion and suction) described above.

Figure 5:
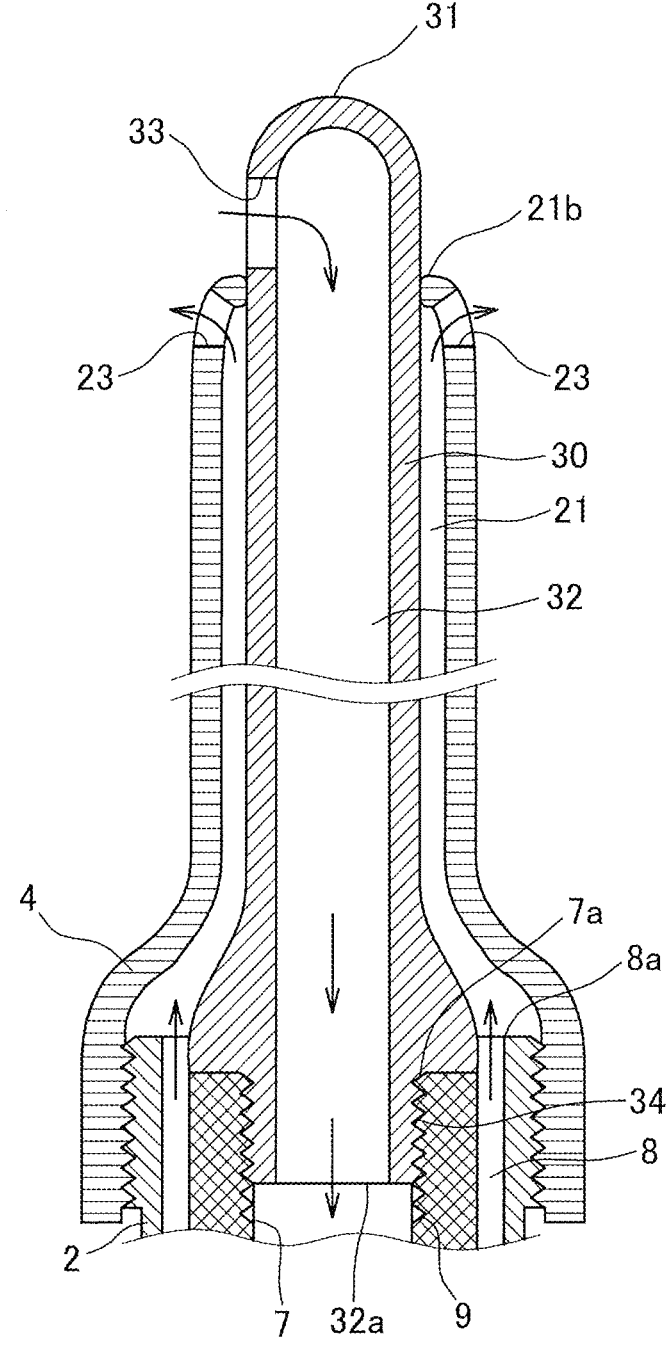
FIG. 5 is a cross-sectional view showing a state where the tip end member for second ophthalmic surgery and the sleeve are attached to the grip portion, and is a cross-sectional view of the tip end side of an instrument for second ophthalmic surgery.

FIG. 4 and FIG. 5 illustrate the tip end member 30 for performing the second treatment. As shown in FIG. 5, the tip end member 30 is formed in an elongated shape, specifically, in a cylindrical shape having a linearly extending single passage 32 therein. A tip end 31 of the tip end member 30 does not have a portion (blade portion, ultrasonic vibration portion, etc.) for crushing, cutting, etc., the treatment part, and is formed in a curved surface shape, for example. A hole 33 is formed in the side surface on the tip end 31 side of the tip end member 30 so as to be connected to the inner passage 32.

The base end side of the tip end member 30 may be formed in the same shape as the tip end member 3 for the first ophthalmic surgery. That is, an opening 32a of the passage 32 is formed at the base end of the tip end member 30. In addition, an external thread portion 34 is formed on the base end opening 32a side of the tip end member 30. The external thread portion 34 can be inserted into the first passage 7 through the first opening 7a of the grip portion 2 and screwed to the internal thread portion 9 of the grip portion 2.

In a state where the tip end member 30 and the sleeve 4 are attached to the grip portion 2, the passage 32 of the tip end member 30 and the first passage 7 of the grip portion 2 are connected to each other via the base end opening 32a of the tip end member 30. In addition, the passage 21 formed between the sleeve 4 and the tip end member 30 and the second passage 8 of the grip portion 2 are connected to each other via the second opening 8a of the grip portion 2. Moreover, the tip end side (tip end 31 and the hole 33) of the tip end member 30 protrudes from the tip end opening 21b of the sleeve 4.

For example, when the above second treatment is performed, the tissue such as cortex of crystalline lens capsule is sucked via the hole 33 and the passage 32 of the tip end member 30 and the first passage 7 of the grip portion 2 while the perfusate is supplied into the eye via the second passage 8 of the grip portion 2 and the passage 21 and the hole 23 in the sleeve 4.

Returning to the description of FIG. 1, the instrument 1 for the first ophthalmic surgery is configured to include the grip portion 2, the tip end member 3, and the sleeve 4 described above. The procedure for combining the respective parts 2 to 4 to obtain the instrument 1 will be described below. First, the grip portion 2, the tip end member 3, and the sleeve 4 in a mutually separated state are prepared. When the tip end member 30 for the second ophthalmic surgery and the sleeve 4 are attached to the grip portion 2 as shown in FIG. 5, the tip end member 30 and the sleeve 4 are detached from the grip portion 2. In this case, first, the sleeve 4 is detached from the grip portion 2 and the tip end member 30 by pulling the sleeve 4 upward in the drawing sheet of FIG. 5. Next, the tip end member 30 is detached from the grip portion 2 by rotating the tip end member 30 around the central axis thereof and unscrewing both thread portions 34 and 9 of the tip end member 30 and the grip portion 2.

After the grip portion 2, the tip end member 3, and the sleeve 4 are prepared, the grip portion 2 is then attached to the tip end member 3. Specifically, both thread portions 9 and 17 of the grip portion 2 and the tip end member 3 are screwed to each other. Next, the sleeve 4 is attached to the grip portion 2 and the tip end member 3. Specifically, the tip end member 3 is inserted into the space 21 through the base end opening 21a side of the sleeve 4 with the tip end side thereof being initially inserted thereinto. Then, the bent portion 16 of the tip end member 3 is caused to protrude from the tip end opening 21b of the sleeve 4, and the attachment portion 22 of the sleeve 4 and the attachment-target portion 10 of the grip portion 2 are engaged with each other. At this time, by moving the sleeve 4 in the direction of the axis L3 or rotating the sleeve 4 around the axis L3, the engagement position of the attachment portion 22 and the attachment-target portion 10 is adjusted, that is, the attachment position of the sleeve 4 in the direction of the axis L3 (in other words, the amount by which the bent portion 16 protrudes from the tip end opening 21*b* of the sleeve 4) is adjusted. In this case, the amount by which the bent portion 16 protrudes from the tip end opening 21*b* of the sleeve 4 may be different from the amount by which the tip end 31 of the tip end member 30 protrudes from the tip end opening 21*b* in FIG. 5, and, for example, may be larger than the amount by which the tip end 31 protrudes from the tip end opening 21*b*. Thus, the instrument 1 is completed.

When the instrument 1 is disassembled into the parts 2, 3, and 4, a procedure that is the reverse of the procedure for combining the parts 2, 3, and 4 may be performed. That is, first, the sleeve 4 is detached from the grip portion 2 and the tip end member 3 by pulling the sleeve 4 upward in the drawing sheet of FIG. 1. Next, the tip end member 3 is detached from the grip portion 2 by rotating the tip end member 3 around the central axis L3 thereof and unscrewing both thread portions 17 and 9 of the tip end member 3 and the grip portion 2. Accordingly, the grip portion 2 can be used for other ophthalmic surgery.

Figure 6:
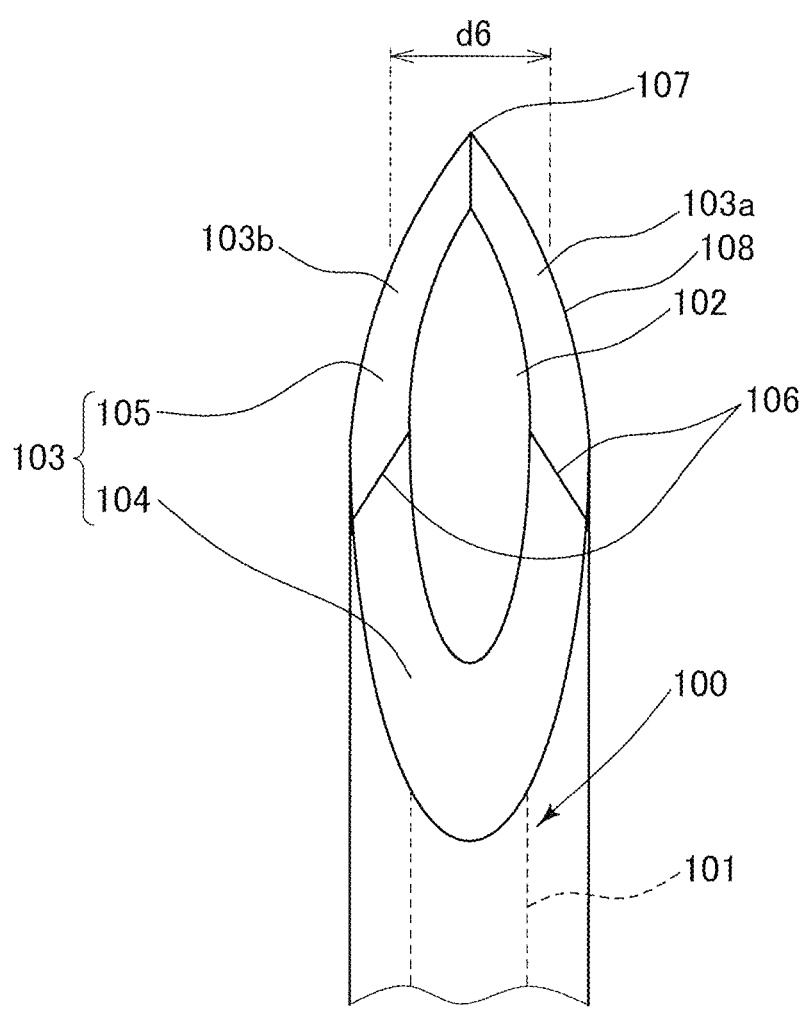
FIG. 6 illustrates the tip end side of a needle member which is the material of the tip end member.

The tip end member 3 may be manufactured, for example, as follows. First, a needle member 100 that is not bent at a tip end thereof as shown in FIG. 6 is prepared. The needle member 100 has therein a passage 101 penetrating from a base end to the tip end thereof. An opening 102 of the passage 101 is formed at the tip end of the needle member 100. The opening 102 and an end surface 103 surrounding the opening 102 are inclined with respect to the central axis of the needle member 100. The end surface 103 is formed in a sharp shape, that is, is a blade surface. The blade surface 103 includes a first blade surface 104 and a second blade surface 105 located on the tip end side with respect to the first blade surface 104. A boundary line 106 between the first blade surface 104 and the second blade surface 105 appears in the blade surface 103. A tip end 107 of the blade surface 103 has a sharp shape, but may have a non-sharp shape. A width between a blade surface 103*b* located on the left side with respect to the opening 102 and a blade surface 103*a* located on the right side with respect to the opening 102 gradually decreases as the distance to the tip end 107 decreases. That is, the tip end side of the needle member 100 has a narrow portion 108 having an outline width d6, in the right-left direction in the drawing sheet of FIG. 6, which gradually decreases toward the tip end 107. The outline width d6 of the narrow portion 108 is smaller than the outer diameter of the needle member 100.

By bending the blade surface 103 (the end surface) of the needle member 100, a portion on the tip end 107 side of the blade surface 103 (specifically, for example, narrow portion 108 (portion of the second blade surface 105)) is bent. This bent portion corresponds to the bent portion 16 of the tip end member 3. In addition, the second blade surface 105 at the bent portion corresponds to the blade surfaces 16*c* and 16*d* (see FIG. 3) of the bent portion 16.

The base end side of the needle member 100 may be processed into the same shape as that of the base end side of the tip end member 3 (i.e., external thread shape) in advance before the tip end side thereof is bent, or may be processed into the same shape as that of the base end side of the tip end member 3 after the tip end side thereof is bent. Thus, the tip end member 3 is obtained.

The instrument 1 is used in, for example, surgery to excise a trabecular meshwork for the treatment of glaucoma as the first ophthalmic surgery. In this case, the suction unit 60 is connected to the first port 11 of the grip portion 2. The liquid supply unit 55 is connected to the second port 12. The practitioner holds the grip portion 2 and inserts the tip end member 3 into the anterior chamber through the outer circumferential portion of the cornea of the eye to be treated. Then, the liquid supply unit 55 is activated to supply the perfusate into the anterior chamber via the second passage 8 of the grip portion 2 and the passage 21 and the hole 23 in the sleeve 4. The supply of the perfusate can inhibit the anterior chamber from shrinking, and can inhibit a large amount of blood from flowing out as a result of the excision of the trabecular meshwork.

The bent portion 16 is placed on the side, of the outer circumference of the anterior chamber, opposite to the outer circumferential portion of the cornea into which the tip end member 3 is inserted. Then, the bent portion 16 is caused to enter the trabecular meshwork while forming a cut serving as a trigger for excision by piercing the trabecular meshwork with the tip end 16*a* of the bent portion 16. Then, by advancing the tip end 16*a* along the outer circumference of the anterior chamber which is the direction in which the trabecular meshwork extends, the trabecular meshwork is excised along this advancement direction with the bent portion 16. At this time, the trabecular meshwork cut with the bent portion 16 is guided by the inner surface of the bent portion 16 and the oblique tip end opening surface 14*a* contiguous therewith, and is pulled out toward the near side. In addition, the suction unit 60 is activated to suck the cut trabecular meshwork via the tip end opening 14 and the passage 13 of the tip end member 3 and the first passage 7 of the grip portion 2 to the suction unit 60. The supply of the perfusate and the suction of the trabecular meshwork may be performed simultaneously, or may be performed at different times during the surgery.

As described above, in this embodiment, the tip end member 3 has the bent-shaped blade portion 16 (bent portion) at the tip end thereof, so that it is easy to excise the trabecular meshwork. In addition, the tip end member 3 is provided separately from the grip portion 2 and is structured to have the single passage 13, so that the structure of the tip end member 3 can be simplified.

Since the grip portion 2 has the first passage 7 and the second passage 8, both the supply of the perfusate and the suction of an excised part such as a trabecular meshwork can be easily performed. Since the grip portion 2 can be used for both the first ophthalmic surgery and the second ophthalmic surgery, convenience can be improved.

Since the attachment position of the sleeve 4 in the axial direction can be adjusted, the sleeve 4 can be used for both the first ophthalmic surgery and the second ophthalmic surgery. For example, in trabeculectomy as the first ophthalmic surgery, it is necessary to place the bent portion 16 on the far side of the anterior chamber from the outer circumferential portion of the cornea into which the tip end member 3 is inserted. By adjusting the attachment position of the sleeve 4 to a lower position in the drawing sheet of FIG. 1, a portion of the instrument 1 (the small-diameter portion 19 of the sleeve 4 and a portion, on the tip end side of the tip end member 3, protruding from the small-diameter portion 19) that can be inserted into the eye can be made longer. Accordingly, it can be made easier to place the bent portion 16 on the far side of the anterior chamber.

Since the sleeve 4 is flexible, it is easy to attach the sleeve 4 to the grip portion 2 and the tip end member 3 or 30. Even if the width d1 (see FIG. 1) of the bent portion 16 is slightly larger than the diameter of the tip end opening 21*b* of the sleeve 4, since the sleeve 4 is flexible, the bent portion 16 can be passed through the tip end opening 21*b* while the tip end opening 21*b* is elastically deformed so as to match the width d1 of the bent portion 16. In addition, by attaching the sleeve 4, the aqueous humor in the eye can be inhibited from coming out even when an incision wound in the cornea for inserting the tip end member 3 into the eye is large.

Figure 7:
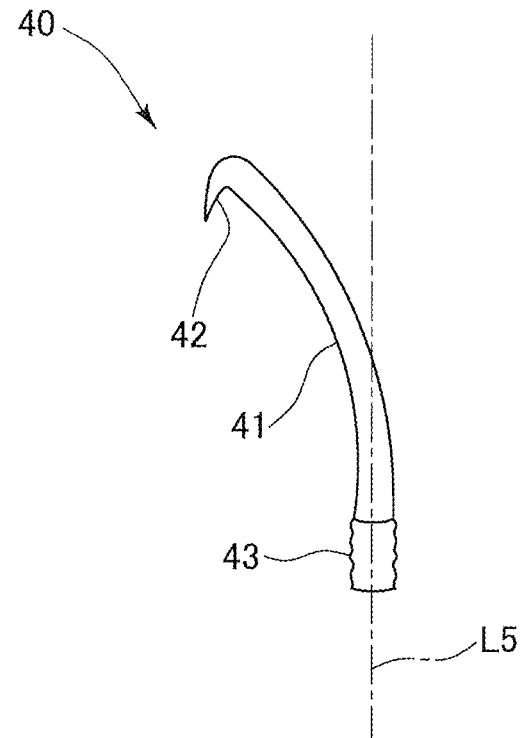
FIG. 7 shows a first modification of the tip end member (intraocular excision member)
Figure 8:
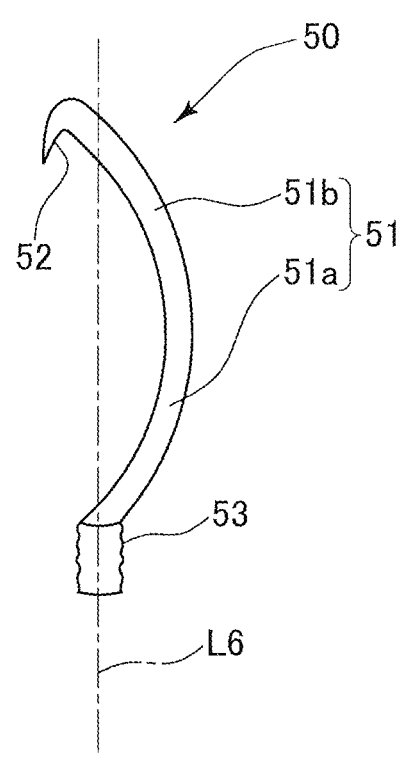
FIG. 8 shows a second modification of the tip end member (intraocular excision member).

This disclosure is not limited to the above embodiment, and various modifications may be made. For example, the above embodiment shows an example in which the body of the tip end member 3 has a linear shape, but the body of the tip end member 3 may be bent as shown in FIG. 7 or FIG. 8. A tip end member 40 in FIG. 7 has a tubular body 41 having a single passage therein, a blade portion 42 provided at the tip end of the body 41 and having a bent shape, and a thread portion 43 provided at the base end of the body 41. The body 41 is bent, and specifically, the body 41 is formed in a curved shape in which the body 41 gradually becomes farther from an axis L5 of the thread portion 43 (in other words, the axis L1 of the grip portion 2 in FIG. 1) as extending from the base end (thread portion 43) toward the tip end (blade portion 42). The blade portion 42 is formed in the same shape as that of the bent portion 16 in FIG. 1 to FIG. 3. The thread portion 43 is formed in the same shape as that of the thread portion 17 in FIG. 1.

A tip end member 50 in FIG. 8 has a tubular body 51 having a single passage therein, a blade portion 52 provided at the tip end of the body 51 and having a bent shape, and a thread portion 53 provided at the base end of the body 51. The body 51 is bent, and specifically has a first portion 51*a* provided on the base end side (thread portion 53 side) thereof, and a second portion 51*b* provided on the tip end side (blade portion 52 side) thereof so as to be contiguous with the first portion 51*a*. The first portion 51*a* is formed in a curved shape in which the first portion 51*a* becomes farther from an axis L6 of the thread portion 53 (in other words, the axis L1 of the grip portion 2 in FIG. 1) as extending from the base end toward the second portion 51*b*. The second portion 51*b* is formed in a curved shape in which the second portion 51*b* gradually approaches the axis L6 as extending toward the tip end side. The blade portion 52 is formed in the same shape as that of the bent portion 16 in FIG. 1 to FIG. 3. The thread portion 53 is formed in the same shape as that of the thread portion 17 in FIG. 1.

The above embodiment shows an example in which the sleeve 4 is attached to the grip portion 2 and the tip end member 3, but the sleeve 4 does not have to be attached thereto. For example, if an incision wound in the cornea is small, the outflow of the aqueous humor in the eye can be suppressed even when the sleeve 4 is not attached. When the sleeve 4 is not attached, ophthalmic surgery may be performed without using the second passage 8 of the grip portion 2.

DESCRIPTION OF THE REFERENCE CHARACTERS 1 ophthalmic surgery instrument
2 grip portion
3, 40, 50 tip end member for first ophthalmic surgery (intraocular excision member)
4 sleeve (outer member)
7 first passage of grip portion
8 second passage of grip portion
9 internal thread portion of grip portion
13 passage of tip end member
14 tip end opening of tip end member
16, 42, 52 bent portion (blade portion)

17, 43, 53 external thread portion of tip end member
30 tip end member for second ophthalmic surgery
What is claimed is:

1. An ophthalmic surgery instrument comprising:
a dual-use grip portion having a first passage and a second passage separately formed therein for performing suction or supply of a perfusate, having a first opening, which is an opening of the first passage, and a second opening, which is an opening of the second passage, formed at a tip end thereof, and used for both first ophthalmic surgery, which is glaucoma surgery, and second ophthalmic surgery different from glaucoma surgery; and
an excision member detachably provided at the tip end of the dual-use grip portion, having a single passage formed therein so as to be connected to the first passage, having a bent-shaped blade portion and an opening of the single passage at a tip end thereof, and used to excise a part in an eye in the first ophthalmic surgery, wherein
the dual-use grip portion has, at the tip end thereof, a thread portion to which the excision member is attached, and
the thread portion is formed so as to be screwable to a tip end member for treating an inside of an eye in the second ophthalmic surgery instead of the excision member.

2. The ophthalmic surgery instrument according to claim 1, further comprising an outer member detachably provided at the tip end of the dual-use grip portion so as to cover an outer side of the excision member in a state where the excision member is attached to the dual-use grip portion, having a tip end opening formed for causing a tip end side of the excision member to protrude therefrom, having a passage formed so as to be connected to the second passage via the second opening, and having an opening of the passage.

3. The ophthalmic surgery instrument according to claim 2, wherein
the outer member includes a large-diameter portion located outside an eye during surgery, and a small-diameter portion formed so as to have a smaller diameter than the large-diameter portion and inserted into the eye during the surgery,
the large-diameter portion has an attachment portion detachably attached to the dual-use grip portion,
the dual-use grip portion has an attachment-target portion to which the attachment portion is attached, and
the attachment portion and the attachment-target portion are formed so as to allow an attachment position of the outer member in an axial direction to be adjusted.

4. The ophthalmic surgery instrument according to claim 2, wherein a width of the blade portion in a direction perpendicular to a central axis of the excision member is smaller than an inner diameter on a tip end side of the outer member.

5. The ophthalmic surgery instrument according to claim 1, wherein
the opening of the excision member is provided such that a central axis of the excision member intersects the opening, and
the blade portion is provided so as to face the opening of the excision member in a direction of the central axis.

6. The ophthalmic surgery instrument according to claim 5, wherein
the blade portion has a blade surface facing the opening side of the excision member, and no blade surface is formed in a surface of the blade portion on a side opposite to the opening side of the excision member.

7. The ophthalmic surgery instrument according to claim 5, wherein the blade portion has a first blade surface, a second blade surface, and an intermediate surface facing the opening side of the excision member, the first blade surface and the second blade surface extend from a base end toward a tip end of the blade portion, an interval between the first blade surface and the second blade surface gradually decreases from the base end toward the tip end of the blade portion, and the intermediate surface is provided between the first blade surface and the second blade surface.

8. An intraocular excision member having a single passage formed therein, having a thread portion at a base end thereof, having a bent-shaped blade portion and an opening of the passage at a tip end thereof, and used to excise a part in an eye in first ophthalmic surgery which is glaucoma surgery, wherein the thread portion is detachably attached to a grip portion held by a user, the grip portion is a dual-use grip portion having a first passage and a second passage separately formed therein for performing suction and supply of a perfusate, having a first opening, which is an opening of the first passage, and a second opening, which is an opening of the second passage, at a tip end thereof, and used for both the first ophthalmic surgery and second ophthalmic surgery different from glaucoma surgery, the grip portion has a thread portion to which the thread portion of the excision member is attached, the thread portion of the grip portion is formed so as to be screwable to a tip end member for treating an inside of an eye in the second ophthalmic surgery instead of the excision member, and the passage of the excision member is connected to the first passage in a state where the excision member is attached to the grip portion.

9. An intraocular excision member manufacturing method for manufacturing the intraocular excision member according to claim 8, comprising:

a preparation step of preparing a needle member which is not bent at a tip end thereof, has therein a passage penetrating from a base end to the tip end thereof, and has an end surface formed in a sharp shape around an opening on the tip end side and inclined with respect to a central axis of the needle member; and a bending step of bending the end surface of the needle member to form the blade portion.

10. The intraocular excision member manufacturing method according to claim 9, wherein the end surface has a narrow portion in which an interval between a blade surface on a right side with respect to the opening and a blade surface on a left side with respect to the opening in the end surface gradually decreases with decreasing a distance to an tip end of the end surface, and the narrow portion is bent in the bending step.

\* \* \* \* \*